(12) United States Patent
Campbell et al.

(10) Patent No.: US 7,883,266 B2
(45) Date of Patent: Feb. 8, 2011

(54) METHOD AND APPARATUS FOR DEFECT DETECTION IN A COLD PLATE

(75) Inventors: Levi A. Campbell, Poughkeepsie, NY (US); Michael J. Domitrovits, New Paltz, NY (US); Michael J. Ellsworth, Jr., Lagrangeville, NY (US); Prabjit Singh, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 495 days.

(21) Appl. No.: 12/053,762

(22) Filed: Mar. 24, 2008

(65) Prior Publication Data

US 2009/0238235 A1  Sep. 24, 2009

(51) Int. Cl.
  *G01N 25/72* (2006.01)
  *G01N 3/00* (2006.01)
  *G01J 5/00* (2006.01)

(52) U.S. Cl. .............. 374/5; 374/57; 374/124; 374/45; 374/137; 374/166; 374/29

(58) Field of Classification Search ......... 374/120, 374/121, 126, 100, 141, 170, 171, 172, 166, 374/110, 111, 112, 115, 137, 130, 33, 145, 374/4, 5, 7, 43–45, 29, 30, 167; 250/339.07, 250/338.01, 339.09, 339.02, 339.04; 345/156, 345/530, 507; 324/760, 765; 361/687; 252/964, 252/960; 378/58, 69; 702/35, 40
See application file for complete search history.

(56) References Cited

U.S. PATENT DOCUMENTS

| | | | | |
|---|---|---|---|---|
| 4,607,341 A | * | 8/1986 | Monchalin | 702/136 |
| 4,696,578 A | * | 9/1987 | Mansuria et al. | 374/45 |
| 4,970,579 A | * | 11/1990 | Arldt et al. | 257/718 |
| 5,580,172 A | * | 12/1996 | Bhardwaj et al. | 374/137 |
| 6,166,777 A | * | 12/2000 | Ock | 348/565 |
| 6,346,704 B2 | | 2/2002 | Kenway | |
| 6,653,730 B2 | | 11/2003 | Chrysler et al. | |
| 6,718,277 B2 | | 4/2004 | Sharma | |
| 6,991,024 B2 | * | 1/2006 | Goodson et al. | 165/80.4 |
| 7,098,079 B2 | | 8/2006 | Chrysler et al. | |
| 7,149,343 B2 | | 12/2006 | Enachescu et al. | |
| 7,173,245 B2 | | 2/2007 | Shakouri et al. | |
| 7,425,093 B2 | * | 9/2008 | Wickersham et al. | 374/5 |

(Continued)

FOREIGN PATENT DOCUMENTS

BE          875803 A  *  8/1979

*Primary Examiner*—Gail Verbitsky
(74) *Attorney, Agent, or Firm*—Geraldine Monteleone, Esq.; Kevin P. Radigan, Esq.; Heslin Rothenberg Farley & Mesiti P.C.

(57) ABSTRACT

Method and apparatus are provided for detecting a defect in a cold plate, configured for cooling an electronics component. The method includes: establishing a first fluid flow through the cold plate, the first fluid flow being at a first temperature; impinging a second fluid flow onto the interface surface, the second fluid flow being at a second temperature, the first temperature and the second temperature being different temperatures; obtaining an isotherm mapping of the interface surface of the cold plate while the first fluid flow passes through the cold plate and the second fluid flow impinges onto the interface surface; and using the isotherm mapping to determine whether the cold plate has a defect. In one embodiment, an infrared-transparent manifold is employed in impinging the second fluid flow onto the interface surface, and the isotherm mapping of the interface surface is obtained through the infrared-transparent manifold.

20 Claims, 11 Drawing Sheets

U.S. PATENT DOCUMENTS

| | | | |
|---|---|---|---|
| 7,581,878 B2 * | 9/2009 | Lee et al. | 374/44 |
| 2007/0247812 A1 * | 10/2007 | Behrens et al. | 361/699 |
| 2009/0024023 A1 * | 1/2009 | Welches et al. | 600/424 |
| 2009/0302880 A1 * | 12/2009 | Potok et al. | 324/765 |
| 2010/0034235 A1 * | 2/2010 | Chen | 374/44 |
| 2010/0175866 A1 * | 7/2010 | Tani et al. | 165/287 |

* cited by examiner

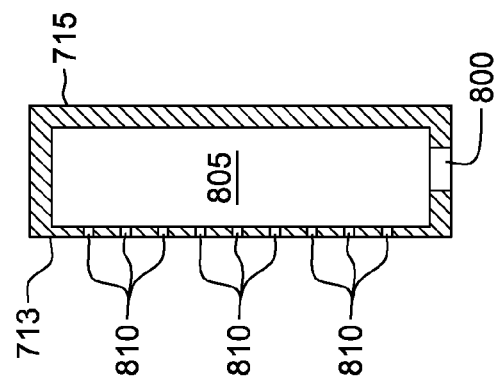
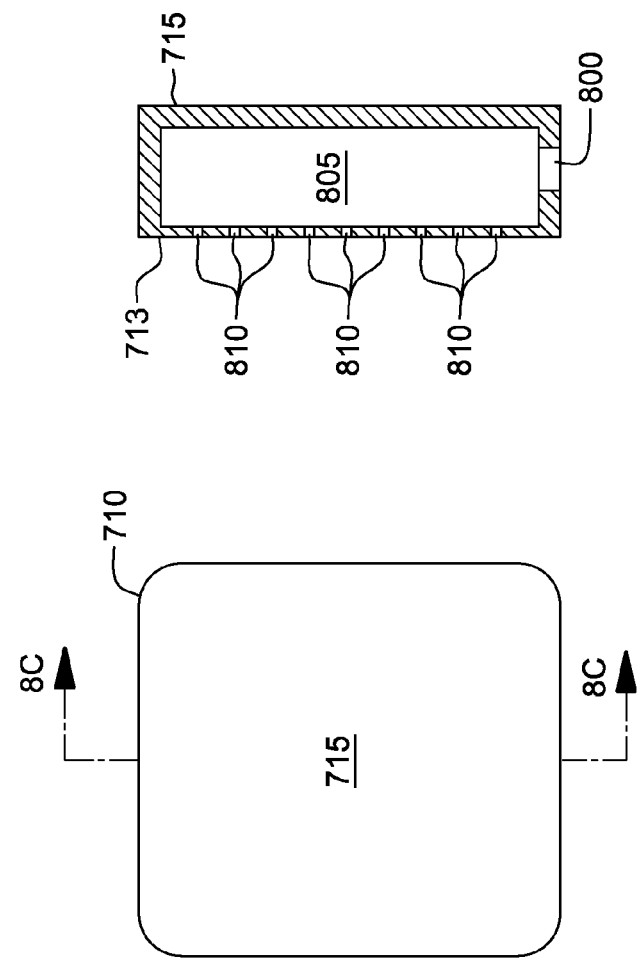
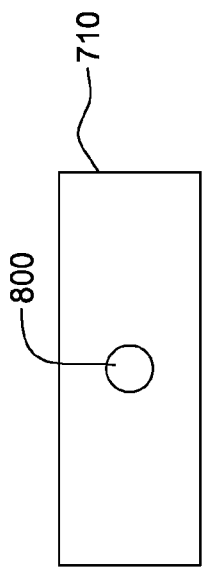

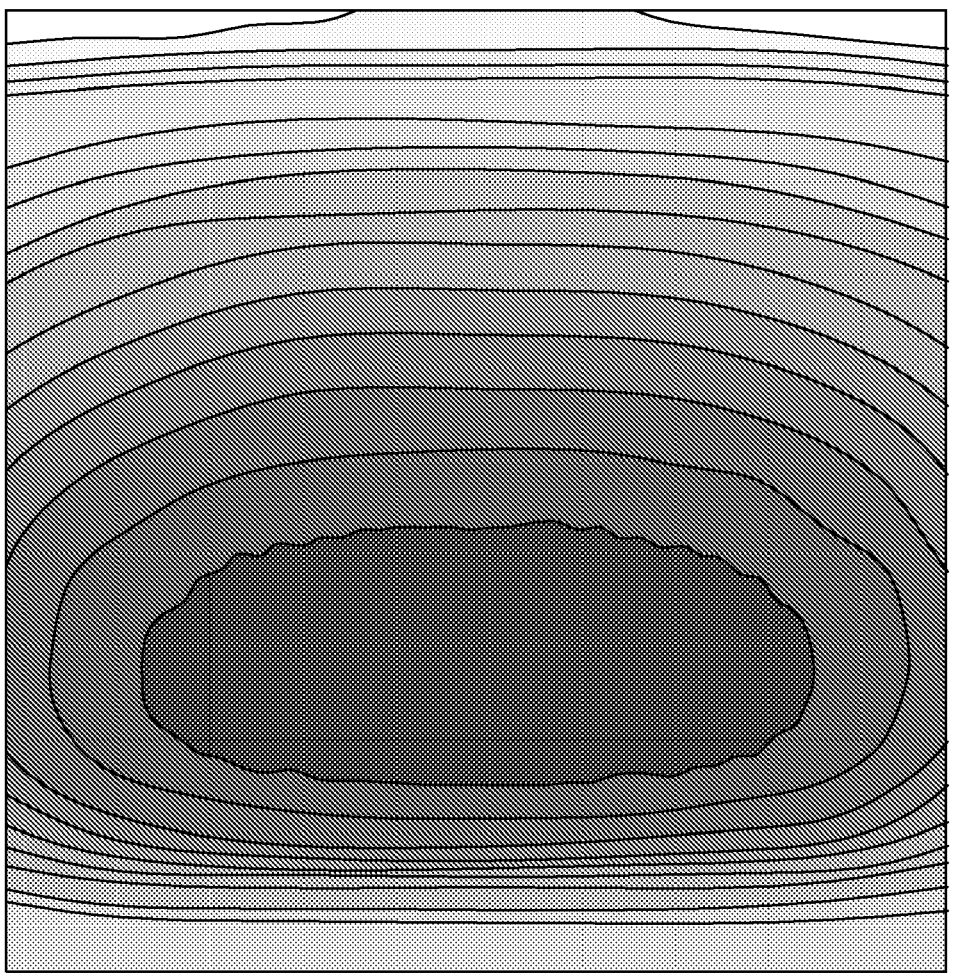
HIGHEST HEAT TRANSFER    LOWEST HEAT TRANSFER
FIG. 10A

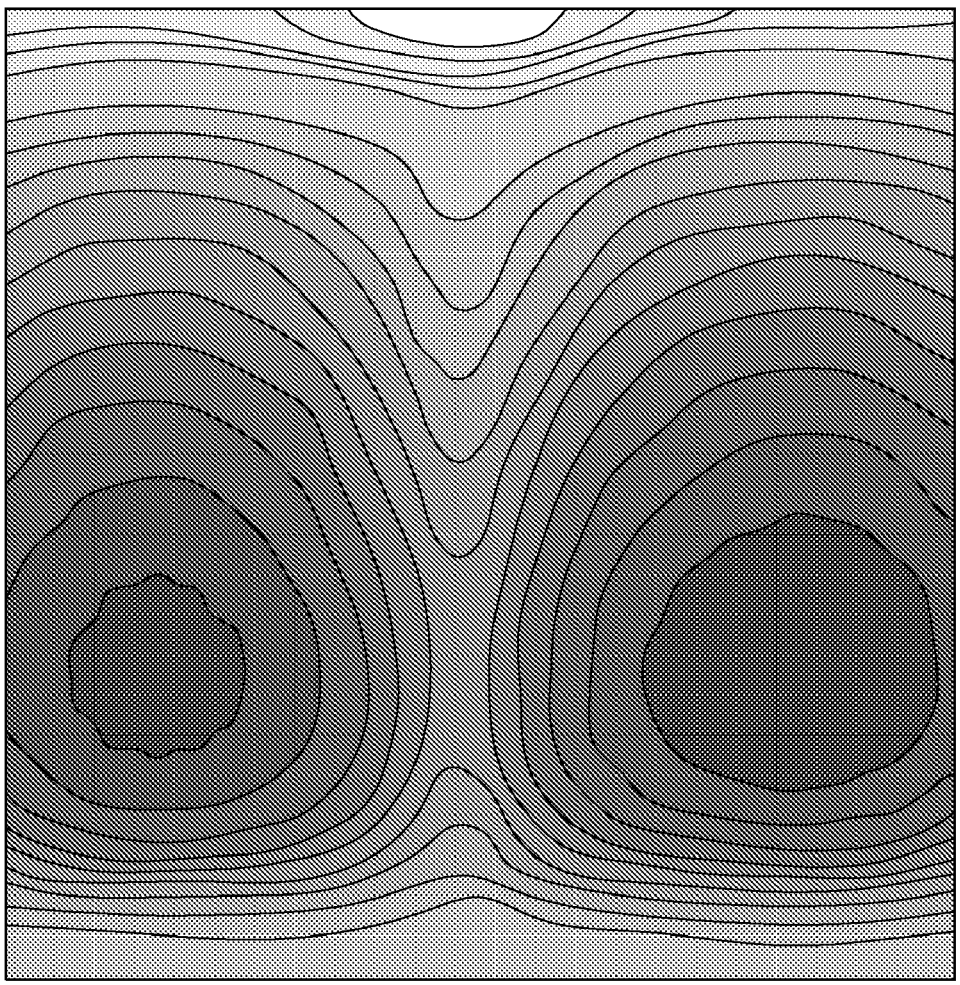
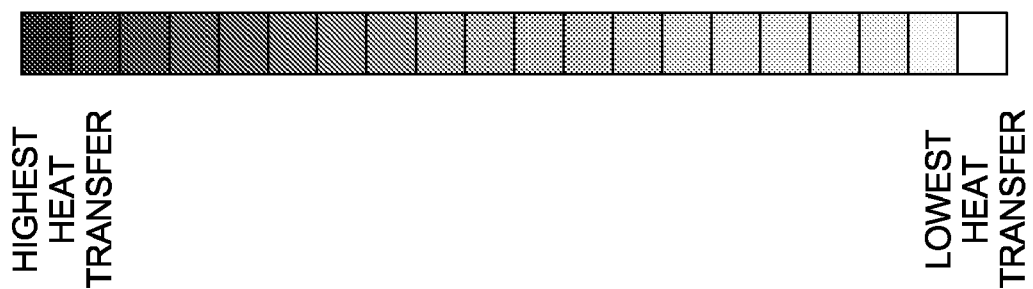
FIG. 10B

METHOD AND APPARATUS FOR DEFECT DETECTION IN A COLD PLATE

TECHNICAL FIELD

The present invention relates in general to systems and methods for facilitating cooling one or more electronic devices of an electronics unit, such as employed in rack-mounted assemblages of individual electronics units, and more particularly, to a method and apparatus for defect detection in a cold plate configured to facilitate cooling of one or more electronic devices.

BACKGROUND OF THE INVENTION

The power dissipation of integrated circuit chips, and the modules containing the chips, continues to increase in order to achieve increases in processor performance. This trend poses a cooling challenge at both the module and system level. Increased airflow rates are needed to effectively cool high power modules and to limit the temperature of the air that is exhausted into a computer center.

In many large server applications, processors along with their associated electronics (e.g., memory, disk drives, power supplies, etc.) are packaged in removable subsystem configurations stacked within a rack or frame. In other cases, the electronics may be in fixed locations within the rack or frame. Typically, the components are cooled by air moving in parallel airflow paths, usually front-to-back, impelled by one or more air moving devices (e.g., fans or blowers). In some cases it may be possible to handle increased power dissipation within a single subsystem by providing greater airflow, through the use of a more powerful air moving device or by increasing the rotational speed (i.e., RPMs) of an existing air moving device. However, this approach is becoming problematic at the rack level in the context of a computer installation (i.e., a data center).

The sensible heat load carried by the air exiting the rack is stressing the ability of the room air-conditioning to effectively handle the load. This is especially true for large installations with "server farms" or large banks of electronics racks close together. One solution to this problem is to combine the air-cooling approach with a liquid-based cooling system employing one or more cold plates coupled to high heat-generating electronic devices (e.g., processor modules) disposed within the electronics subsystems of the electronics rack. Although advantageous, a defect in one or more of the cold plates, such as a blocked coolant channel in a cold plate, can degrade cooling capacity of such a combined cooling approach.

SUMMARY OF THE INVENTION

One approach to evaluating a cold plate for a defect is to employ radiography. Unfortunately, a radiographic approach to defect detection in a cold plate requires expensive equipment, is time consuming, and it is difficult to achieve reliable results on a complex cold plate structure, being a subjective approach.

Another approach, comprising an aspect of the present invention, is a method of detecting a defect in a cold plate, which includes: establishing a first fluid flow through the cold plate, the first fluid flow being at a first temperature, wherein the cold plate is configured to facilitate cooling of an electronics component when an interface surface thereof is coupled to the electronics component; impinging a second fluid flow onto the interface surface of the cold plate, the second fluid flow being at a second temperature, wherein the second temperature and first temperature are different temperatures; obtaining an isotherm mapping of the interface surface of the cold plate while the first fluid flow passes through the cold plate and the second fluid flow impinges onto the interface surface; and using the isotherm mapping in determining whether the cold plate has a defect.

In another aspect, an apparatus for detecting a defect in a cold plate is provided. The apparatus includes a first fluid flow supply, a manifold, and a thermal imaging device. The first fluid flow supply is coupled to establish a first fluid flow through the cold plate, the first fluid flow being at a first temperature, wherein the cold plate is configured to facilitate cooling of an electronics device when an interface surface thereof is coupled to the electronics component and coolant is passed therethrough. The manifold is configured to impinge a second fluid flow onto the interface surface of the cold plate, wherein the second fluid flow is at a second temperature, the first and second temperatures being different temperatures. The thermal imaging device is positioned to obtain an isotherm mapping of the interface surface of the cold plate while the first fluid flow passes through the cold plate and the second fluid flow impinges onto the interface surface. This isotherm mapping is then utilized to determine whether the cold plate has a defect.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 8A-8C illustrate one embodiment of infrared-transparent manifold employed in the apparatus of FIG. 7, in accordance with an aspect of the present invention;

FIG. 10A is a graphical example of a predetermined reference isotherm mapping of a cold plate, in accordance with an aspect of the present invention; and FIG. 10B is a graphical example of an isotherm mapping of a cold plate having a defect comprising, for example, one or more blocked channels in the cold plate, detected in accordance with an aspect of the present invention.

DETAILED DESCRIPTION OF THE INVENTION

Figure 1:
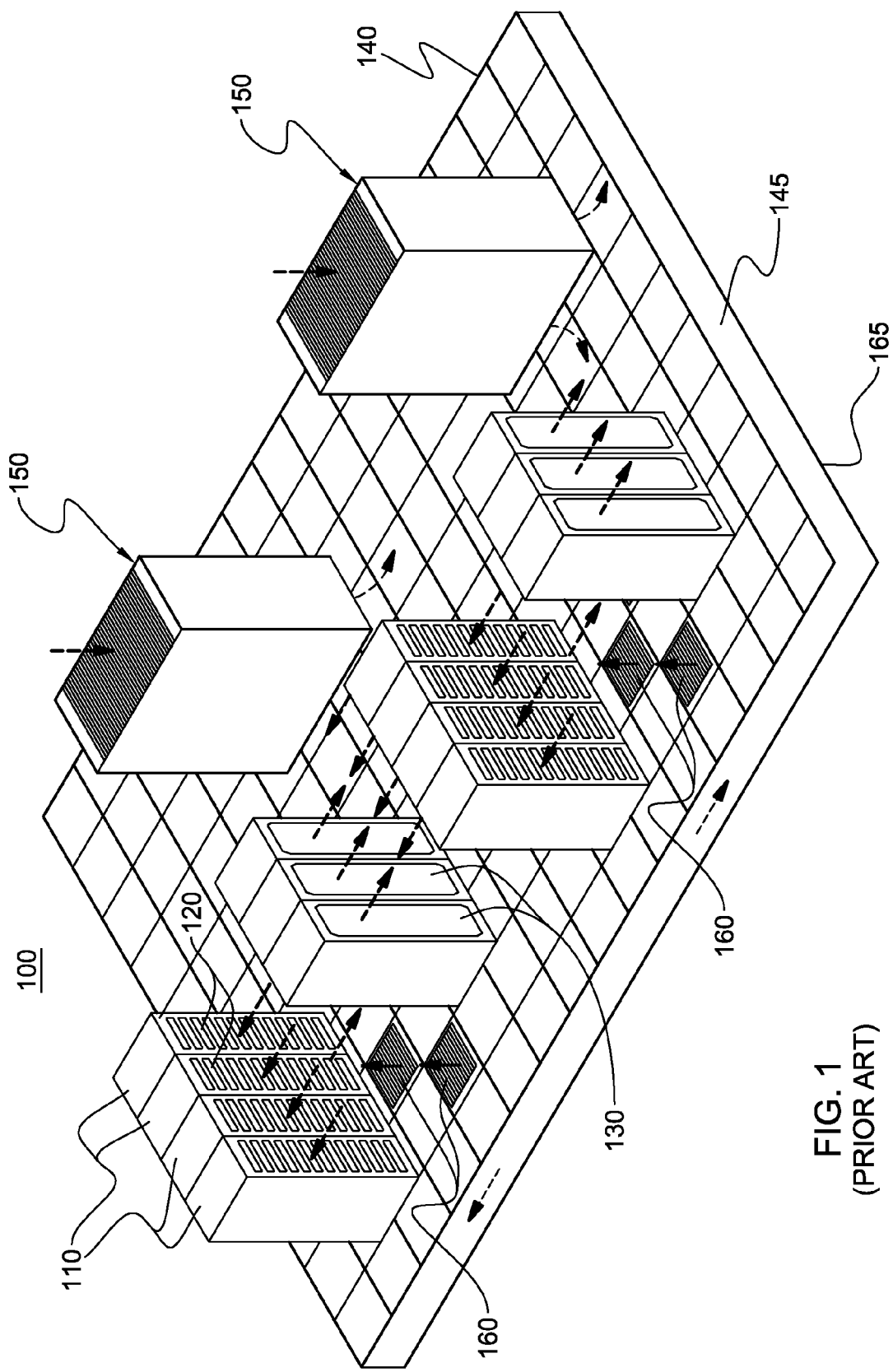
FIG. 1 depicts one embodiment of a conventional raised floor layout of an air-cooled data center.

As used herein, the terms "electronics rack", "rack-mounted electronic equipment", and "rack unit" are used interchangeably, and unless otherwise specified include any housing, frame, rack, compartment, blade server system, etc., having one or more heat generating components of a computer system or electronics system, and may be, for example, a stand alone computer processor having high, mid or low end processing capability. In one embodiment, an electronics rack may comprise multiple electronics subsystems or drawers, each having one or more heat generating components disposed therein requiring cooling. "Electronics subsystem" refers to any sub-housing, blade, book, drawer, node, compartment, etc., having one or more heat generating electronic devices disposed therein. Each electronics subsystem of an electronics rack may be movable or fixed relative to the electronics rack, with the rack-mounted electronics drawers and blades of a blade center system being two examples of subsystems of an electronics rack to be cooled.

"Electronic device" refers to any heat generating electronic device of, for example, a computer system or other electronics unit requiring cooling. By way of example, an electronic device may comprise one or more integrated circuit dies and/or other electronic devices to be cooled, including one or more processor dies, memory dies and memory support dies. As a further example, the electronic device may comprise one or more bare dies or one or more packaged dies disposed on a common carrier. As used herein, "primary heat generating component" refers to a primary heat generating electronic device within an electronics subsystem, while "secondary heat generating component" refers to an electronic device of the electronics subsystem generating less heat than the primary heat generating component to be cooled. "Primary heat generating die" refers, for example, to a primary heat generating die or chip within a heat generating electronic device comprising primary and secondary heat generating dies (with a processor die being one example). "Secondary heat generating die" refers to a die of a multi-die electronic device generating less heat than the primary heat generating die thereof (with memory dies and memory support dies being examples of secondary dies to be cooled). As one example, a heat generating electronic device could comprise multiple primary heat generating bare dies and multiple secondary heat generating dies on a common carrier. Further, the term "cold plate" refers to any thermally conductive structure having one or more channels or passageways formed therein for flowing of coolant therethrough. In addition, "metallurgically bonded" refers generally herein to two components being welded, brazed or soldered together by any means.

As used herein, a "liquid-to-liquid heat exchanger" may comprise, for example, two or more coolant flow paths, formed of thermally conductive tubing (such as copper or other tubing) in thermal or mechanical contact with each other. Size, configuration and construction of the liquid-to-liquid heat exchanger can vary without departing from the scope of the invention disclosed herein. Further, "data center" refers to a computer installation containing one or more electronics racks to be cooled. As a specific example, a data center may include one or more rows of rack-mounted computing units, such as server units.

One example of facility coolant and system coolant is water. However, the cooling concepts disclosed herein are readily adapted to use with other types of coolant on the facility side and/or on the system side. For example, one or more of the coolants may comprise a brine, a fluorocarbon liquid, a liquid metal, or other similar coolant, or refrigerant, while still maintaining the advantages and unique features of the present invention.

Reference is made below to the drawings, which are not drawn to scale to facilitate understanding thereof, wherein the same reference numbers used throughout different figures designate the same or similar components.

FIG. 1 depicts a raised floor layout of an air cooled data center 100 typical in the prior art, wherein multiple electronics racks 110 are disposed in one or more rows. A data center such as depicted in FIG. 1 may house several hundred, or even several thousand microprocessors. In the arrangement illustrated, chilled air enters the computer room via perforated floor tiles 160 from a supply air plenum 145 defined between the raised floor 140 and a base or sub-floor 165 of the room. Cooled air is taken in through louvered covers at air inlet sides 120 of the electronics racks and expelled through the back (i.e., air outlet sides 130) of the electronics racks. Each electronics rack 110 may have one or more air moving devices (e.g., fans or blowers) to provide forced inlet-to-outlet airflow to cool the electronic devices within the subsystem(s) of the rack. The supply air plenum 145 provides conditioned and cooled air to the air-inlet sides of the electronics racks via perforated floor tiles 160 disposed in a "cold" aisle of the computer installation. The conditioned and cooled air is supplied to plenum 145 by one or more air conditioning units 150, also disposed within the data center 100. Room air is taken into each air conditioning unit 150 near an upper portion thereof. This room air comprises in part exhausted air from the "hot" aisles of the computer installation defined, for example, by opposing air outlet sides 130 of the electronics racks 110.

Due to the ever-increasing airflow requirements through electronics racks, and the limits of air distribution within the typical data center installation, liquid-based cooling is being combined with the conventional air-cooling. FIGS. 2-5 illustrate one embodiment of a liquid-based cooling system employing one or more cold plates coupled to high heat-generating electronic devices disposed within the electronics racks.

Figure 2:
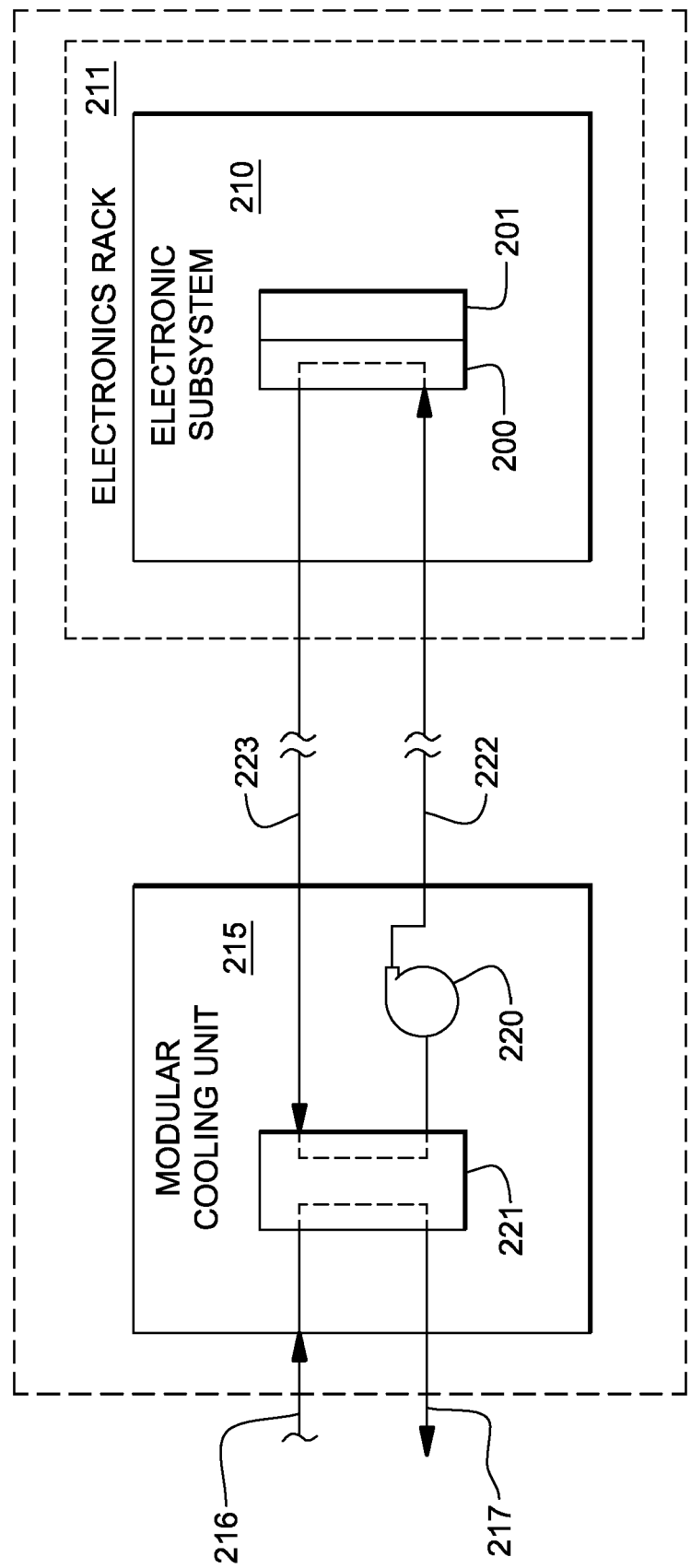
FIG. 2 is a schematic of one embodiment of an electronics subsystem of an electronics rack, wherein an electronics component is liquid-cooled by system coolant provided by one or more modular cooling units to one or more liquid-cooled cold plates, in accordance with an aspect of the present invention.

FIG. 2 schematically illustrates operation of such a liquid-based cooling system, wherein a liquid cooled cold plate 200 is shown coupled to an electronics module or component 201 of electronics subsystem 210 within the electronics rack 211. Heat is removed from electronics module 201 via the system coolant circulated via pump 220 through cold plate 200 within the system coolant loop defined by liquid-to-liquid heat exchanger 221 of modular cooling unit 215, lines 222, 223 and cold plate 200. The system coolant loop and modular cooling unit are designed to provide coolant of a controlled temperature and pressure, as well as controlled chemistry and cleanliness to the electronics module(s). Furthermore, the system coolant is physically separate from the less controlled facility coolant in lines 216, 217 to which heat is ultimately transferred.

Figure 3:
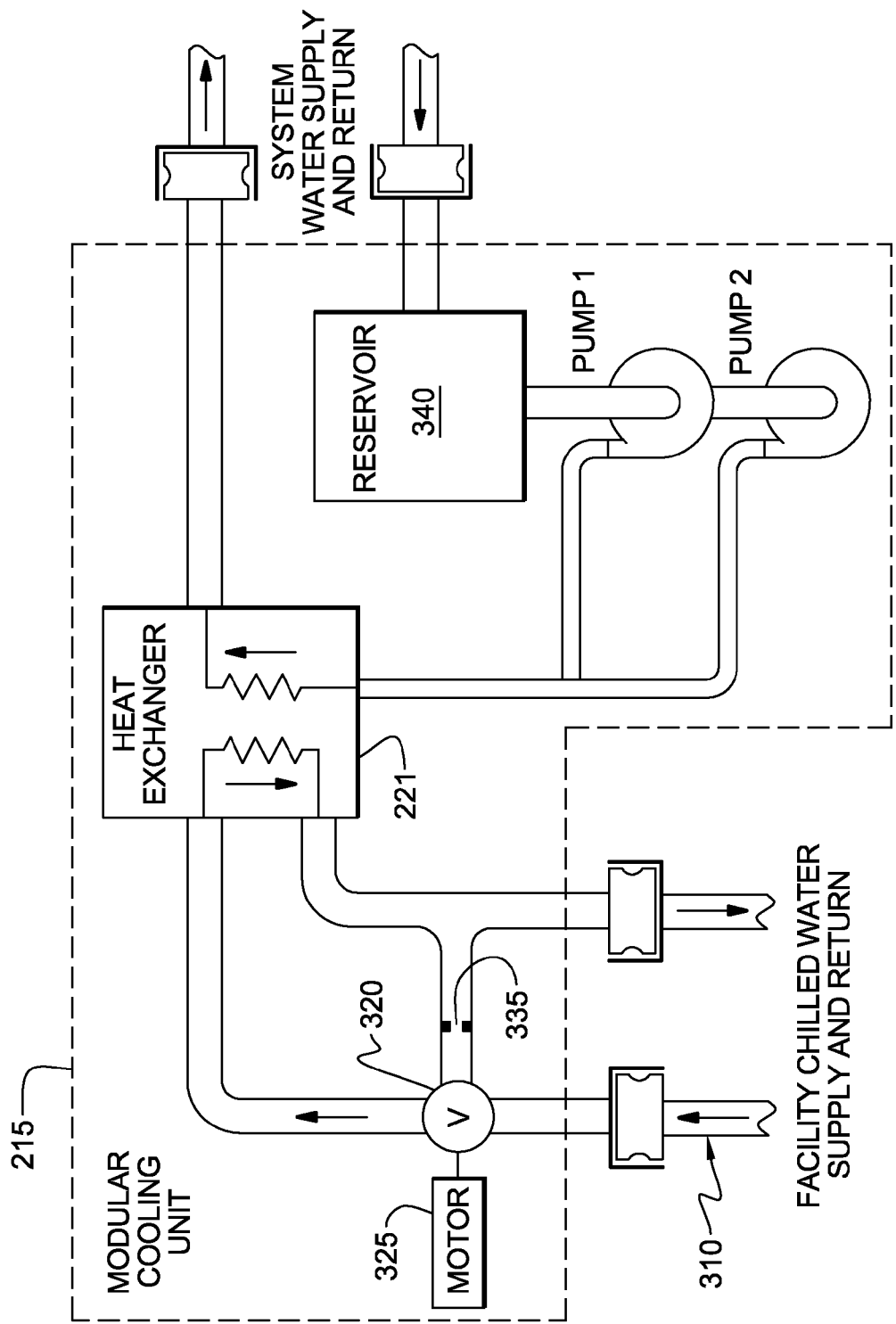
FIG. 3 is a schematic of one embodiment of the modular cooling unit of FIG. 2, in accordance with an aspect of the present invention.

FIG. 3 depicts a more detailed embodiment of a modular cooling unit 215, in accordance with an aspect of the present invention. As shown in FIG. 3, modular cooling unit 215 includes a first cooling loop wherein chilled, facility coolant is supplied 310 and passes through a control valve 320 driven by a motor 325. Valve 320 determines an amount of facility coolant to be passed through a heat exchanger 221, with a portion of the facility coolant possibly being returned directly via a bypass orifice 335. The modular cooling unit further includes a second cooling loop with a reservoir tank 340 from which system coolant is pumped, either by pump 1 or pump 2, into the heat exchanger 221 for conditioning and output thereof as cooled system coolant to the electronics rack to be cooled within the docking station. The cooled system coolant is supplied to one or more cooling systems within one or more electronics drawers of the electronics rack via the shared supply and return manifolds.

Figure 4:
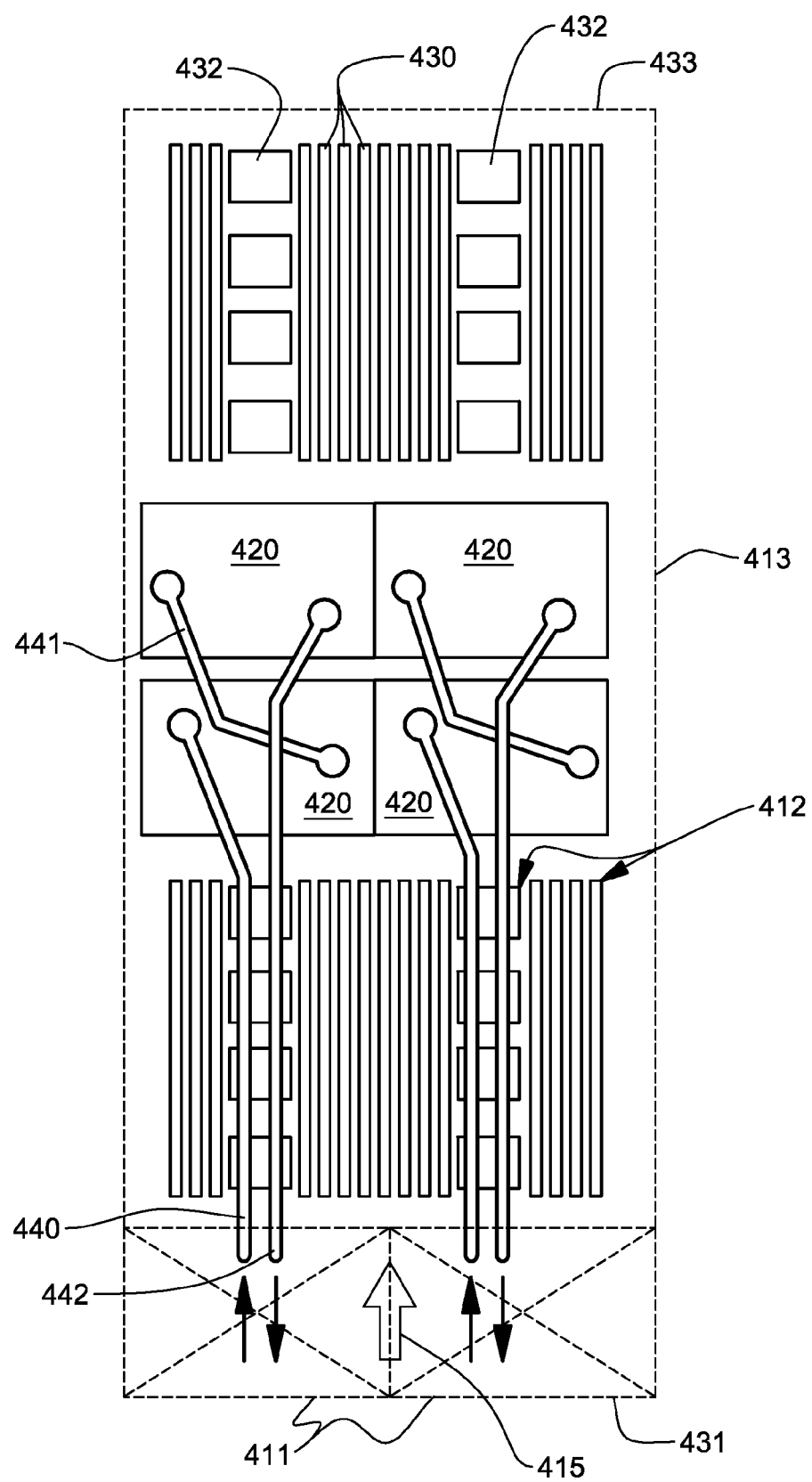
FIG. 4 is a plan view of one embodiment of an electronics subsystem layout illustrating an air and liquid cooling system for cooling components of the electronics subsystem, in accordance with an aspect of the present invention.

FIG. 4 depicts one embodiment of an electronics subsystem 413 component layout wherein one or more air moving devices 411 provide forced air flow 415 to cool multiple components 412 within electronics subsystem 413. Cool air is taken in through a front 431 and exhausted out a back 433 of the subsystem. The multiple components to be cooled include multiple processor modules to which liquid-cooled cold plates 420 (of a liquid-based cooling system) are coupled, as well as multiple arrays of memory modules 430 (e.g., dual in-line memory modules (DIMMs)) and multiple rows of memory support modules 432 (e.g., DIMM control modules) to which air-cooled heat sinks are coupled. In the embodiment illustrated, memory modules 430 and the memory support modules 432 are partially arrayed near front 431 of electronics subsystem 413, and partially arrayed near back 433 of electronics subsystem 413. Also, in the embodiment of FIG. 4, memory modules 430 and the memory support modules 432 are cooled by air flow 415 across the electronics subsystem.

The illustrated liquid-based cooling system further includes multiple coolant-carrying tubes connected to and in fluid communication with liquid-cooled cold plates 420. The coolant-carrying tubes comprise sets of coolant-carrying tubes, with each set including (for example) a coolant supply tube 440, a bridge tube 441 and a coolant return tube 442. In this example, each set of tubes provides liquid coolant to a series-connected pair of cold plates 420 (coupled to a pair of processor modules). Coolant flows into a first cold plate of each pair via the coolant supply tube 440 and from the first cold plate to a second cold plate of the pair via bridge tube or line 441, which may or may not be thermally conductive. From the second cold plate of the pair, coolant is returned through the respective coolant return tube 442.

Figure 5:
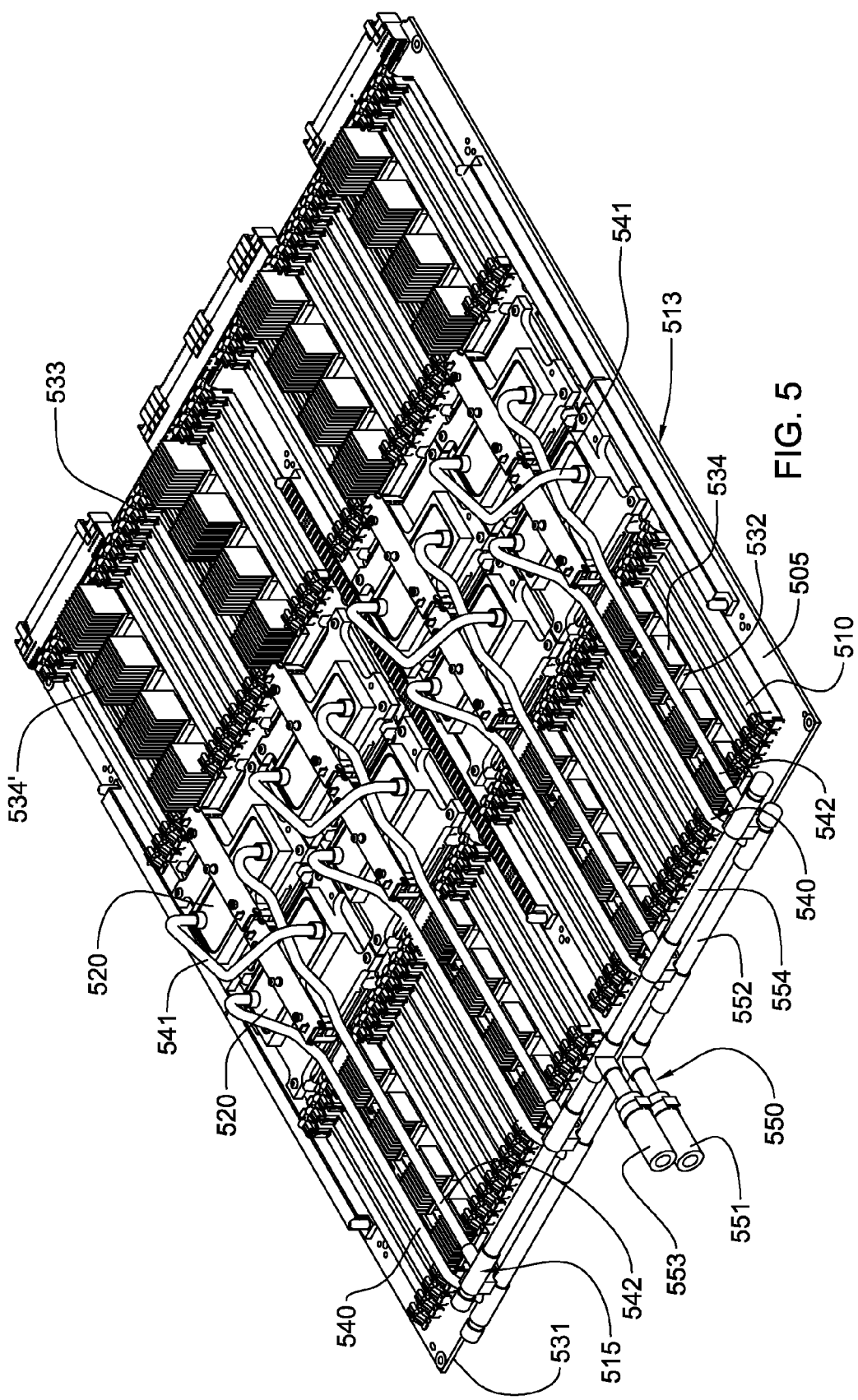
FIG. 5 depicts one detailed embodiment of a partially assembled electronics subsystem layout, wherein the electronics subsystem includes eight heat-generating electronics device to be actively cooled, each having a respective liquid-cooled cold plate of a liquid-based cooling system coupled thereto, in accordance with an aspect of the present invention.

FIG. 5 depicts in greater detail an alternate electronics subsystem layout comprising eight processor modules, each having a respective liquid-cooled cold plate of a liquid-based cooling system coupled thereto. The liquid-based cooling system is shown to further include associated coolant-carrying tubes for facilitating passage of liquid coolant through the liquid-cooled cold plates and a header subassembly to facilitate distribution of liquid coolant to and return of liquid coolant from the liquid-cooled cold plates. By way of specific example, the liquid coolant passing through the liquid-based cooling subsystem is chilled water.

FIG. 5 is an isometric view of one embodiment of an electronics subsystem or drawer and monolithic cooling system, in accordance with an aspect of the present invention. The depicted planar server assembly includes a multi-layer printed circuit board to which memory DIMM sockets and various electronic devices to be cooled are attached both physically and electrically. In the cooling system depicted, a supply header is provided to distribute liquid coolant from a single inlet to multiple parallel coolant flow paths and a return header collects exhausted coolant from the multiple parallel coolant flow paths into a single outlet. Each parallel coolant flow path includes one or more cold plates in series flow arrangement to cool one or more electronic devices to which the cold plates are mechanically and thermally coupled. The number of parallel paths and the number of series-connected liquid-cooled cold plates depends, for example, on the desired device temperature, available coolant temperature and coolant flow rate, and the total heat load being dissipated from each electronic device.

More particularly, FIG. 5 depicts a partially assembled electronics subsystem 513 and an assembled liquid-based cooling system 515 coupled to primary heat generating components (e.g., including processor dies) to be cooled. In this embodiment, the electronics system is configured for (or as) an electronics drawer of an electronics rack, and includes, by way of example, a support substrate or planar board 505, a plurality of memory module sockets 510 (with the memory modules (e.g., dual in-line memory modules) not shown), multiple rows of memory support modules 532 (each having coupled thereto an air-cooled heat sink 534), and multiple processor modules (not shown) disposed below the liquid-cooled cold plates 520 of the liquid-based cooling system 515.

In addition to liquid-cooled cold plates 520, liquid-based cooling system 515 includes multiple coolant-carrying tubes, including coolant supply tubes 540 and coolant return tubes 542 in fluid communication with respective liquid-cooled cold plates 520. The coolant-carrying tubes 540, 542 are also connected to a header (or manifold) subassembly 550 which facilitates distribution of liquid coolant to the coolant supply tubes and return of liquid coolant from the coolant return tubes 542. In this embodiment, the air-cooled heat sinks 534 coupled to memory support modules 532 closer to front 531 of electronics subsystem 513 are shorter in height than the air-cooled heat sinks 534' coupled to memory support modules 532 near back 533 of electronics subsystem 513. This size difference is to accommodate the coolant-carrying tubes 540, 542 since, in this embodiment, the header subassembly 550 is at the front 531 of the electronics drawer and the multiple liquid-cooled cold plates 520 are in the middle of the drawer.

Liquid-based cooling system 515 comprises a pre-configured monolithic structure which includes multiple (pre-assembled) liquid-cooled cold plates 520 configured and disposed in spaced relation to engage respective heat generating electronic devices. Each liquid-cooled cold plate 520 includes, in this embodiment, a liquid coolant inlet and a liquid coolant outlet, as well as an attachment subassembly (i.e., a cold plate/load arm assembly). Each attachment subassembly is employed to couple its respective liquid-cooled cold plate 520 to the associated electronic device to form the cold plate and electronic device assemblies. Alignment openings (i.e., thru-holes) are provided on the sides of the cold plate to receive alignment pins or positioning dowels during the assembly process. Additionally, connectors (or guide pins) are included within attachment subassembly which facilitate use of the attachment assembly.

As shown in FIG. 5, header subassembly 550 includes two liquid manifolds, i.e., a coolant supply header 552 and a coolant return header 554, which in one embodiment, are coupled together via supporting brackets. In the monolithic cooling structure of FIG. 5, the coolant supply header 552 is metallurgically bonded in fluid communication to each coolant supply tube 540, while the coolant return header 554 is metallurgically bonded in fluid communication to each coolant return tube 552. A single coolant inlet 551 and a single coolant outlet 553 extend from the header subassembly for coupling to the electronics rack's coolant supply and return manifolds (not shown).

FIG. 5 also depicts one embodiment of the pre-configured, coolant-carrying tubes. In addition to coolant supply tubes 540 and coolant return tubes 542, bridge tubes or lines 541 are provided for coupling, for example, a liquid coolant outlet of one liquid-cooled cold plate to the liquid coolant inlet of another liquid-cooled cold plate to connect in series fluid flow the cold plates, with the pair of cold plates receiving and returning liquid coolant via a respective set of coolant supply and return tubes. In one embodiment, the coolant supply tubes 540, bridge tubes 541 and coolant return tubes 542 are each pre-configured, semi-rigid tubes formed of a thermally conductive material, such as copper or aluminum, and the tubes are respectively brazed, soldered or welded in a fluid-tight manner to the header subassembly and/or the liquid-cooled cold plates. The tubes are pre-configured for a particular electronics system to facilitate installation of the monolithic structure in engaging relation with the electronics system.

The liquid-cooled cold plates of the above-described liquid-based cooling system typically have coolant, such as water, flowing through narrow channels. For optimum cooling performance, these narrow channels of the cold plate must not be blocked. A blocked channel has limited cooling capability, since coolant cannot flow therethrough. Thus, a need exists in the art for insuring that the cold plate is free of defects, such as one or more blocked channels.

Figure 6:
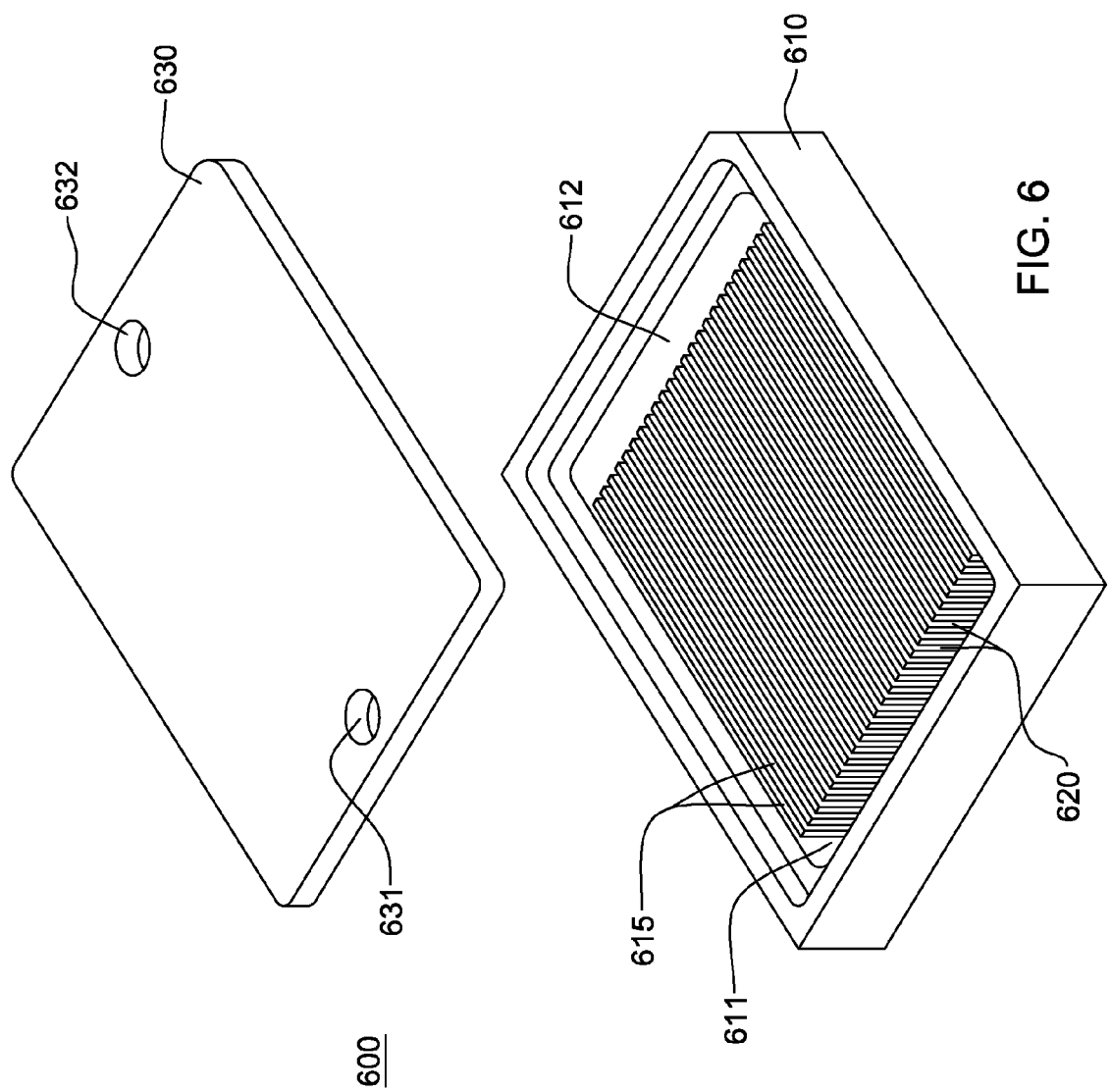
FIG. 6 is a partially exploded isometric view of one embodiment of a liquid-cooled cold plate to be tested for a defect, in accordance with an aspect of the present invention.

FIG. 6 illustrates one embodiment of a cold plate to undergo defect detection testing, in accordance with an aspect of the present invention. This cold plate, generally denoted 600, includes a thermally conductive base 610 having a plurality of thermally conductive plate fins 615 disposed therein defining a plurality of channels 620 through which coolant flows from a coolant inlet plenum 611 to a coolant outlet plenum 612. In this example, the plurality of channels 620 are straight channels extending between the coolant inlet plenum 611 and coolant outlet plenum 612 of the cold plate. A lid 630 is, for example, to be metallurgically bonded to base 610, and includes a coolant inlet port 631 and a coolant outlet port 632, each in fluid communication with a respective one of the coolant inlet plenum 611 and coolant outlet plenum 612. As one example, base 610 and lid 630 are each fabricated of metal, such as copper or aluminum. During fabrication, metallurgically bonding lid 630 to base 610 might result in, for example, braze or solder blocking one or more channels of the plurality of channels 620, detection of which is addressed by the concepts presented herein.

Those skilled in the art should note that cold plate 600 of FIG. 6 is provided herein by way of example only. The concepts presented are not limited to the particular configuration of cold plate. For example, more or less channels may be employed within the cold plate, and the channel(s) configuration may vary, without departing from the scope of the invention presented.

Figure 7:
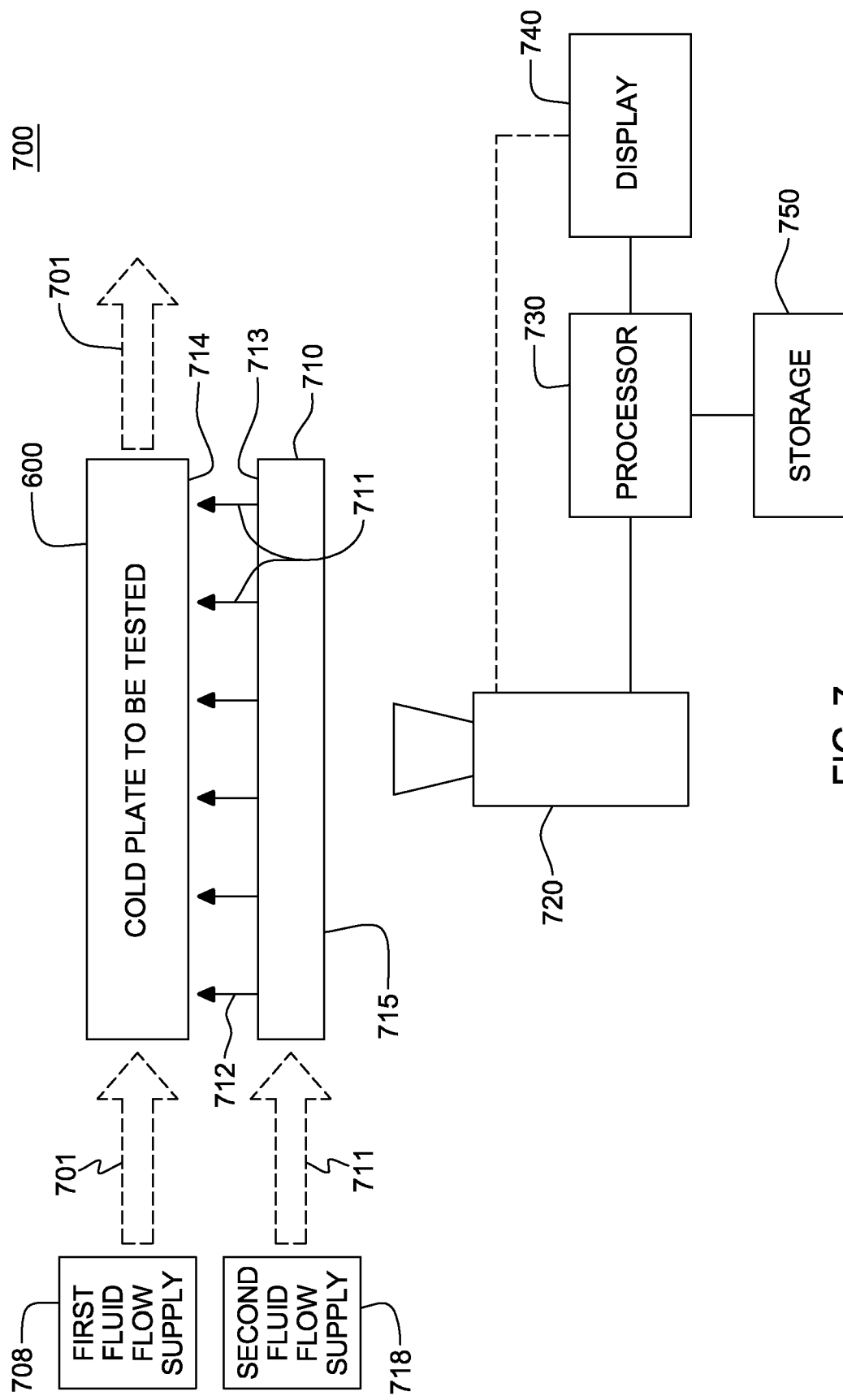
FIG. 7 depicts one embodiment of an apparatus for detecting a defect in a cold plate, in accordance with an aspect of the present invention.

FIG. 7 depicts one example of an apparatus, generally denoted 700, for detecting a defect in a cold plate, in accordance with an aspect of the present invention. As depicted, apparatus 700 includes a first fluid flow supply 708 for providing a first fluid flow 701 through cold plate 600, and a second fluid flow supply 718 for providing a second fluid flow 711 onto the cold plate via a manifold 710. Manifold 710 includes a plurality of orifices (e.g., jet orifices) in a main surface 713 thereof which are disposed to impinge the second fluid flow 711 onto an interface surface 714 of cold plate 600. In this example, interface surface 714 is the surface of the cold plate configured to couple to the electronic device to be cooled. In accordance with an aspect of the present invention, the first fluid flow is provided at a first temperature and the second fluid flow is provided at a second temperature, wherein the first and second temperatures are different temperatures. By way of example, the first and second temperatures differ by at least 20° C. for a typical cold plate to be tested, assuming that the cold plate is made of copper, the base thickness is nearly equal to the fin spacing and the first and second fluid are air. In other situations, the temperature difference required will vary based on several factors: a thicker base or narrower fin spacing will require a larger temperature difference, as will choosing a cold plate material with a lower conductivity (such as aluminum), or using an imaging system with lower than the current state of the art resolution, while the use of a first and second fluid of higher thermal conductivity, density and specific heat (such as water) will not require as large a temperature difference.

The first fluid flow and the second fluid flow may comprise the same or different fluids. For example, air or other gas, or a liquid such as water, may be employed in establishing the first fluid flow and/or the second fluid flow. As one example, the first fluid flow and second fluid flow each comprise air flows of different temperatures. For example, the first fluid flow might be a hot air flow, and the second fluid flow a cold air flow. Alternatively, the first fluid flow could be a cold air flow, and the second fluid flow a hot air flow. Advantageously, the use of air or other gas as the first fluid flow avoids the need to subsequently drain liquid from the cold plate after the testing operation.

In the embodiment illustrated in FIG. 7, manifold 715 is an infrared-transparent manifold and a thermal imaging device 720, such as an infrared camera, is employed to obtain an isotherm mapping of interface surface 714 through the infrared-transparent manifold while the first fluid flow passes through the cold plate and the second fluid flow impinges on the interface surface. As one example, thermal imaging device 720 might be a ThermoVision A320 infrared camera, available from FLIP Systems, of Boston, Mass., or a Fluke Ti series infrared camera, available from Fluke Corp., of Everett, Wash. Deviation in the resultant isotherm mapping of the interface surface from a reference or anticipated mapping is an indication of a defect in the cold plate, such as a blocked channel. Evaluation of the isotherm mapping can be either manual or automatic. If manual, an isotherm mapping of the interface surface may be output directly to a display 740 for operator viewing. Alternatively, an automated approach may be implemented employing a processor 730 and isotherm map storage 750 to compare the isotherm mapping to one or more predetermined, stored reference mappings produced from a known good cold plate.

In one embodiment, available x-ray radiographic tools could be employed to facilitate this automated comparison of the isotherm mapping to a predetermined reference mapping. For example, Clemex Vision PE image analysis software, from Clemex, Longueuil, Canada, may be employed. If the isotherm mapping is equivalent to the predetermined reference mapping (for example, has contours within a predefined acceptable deviation from the predetermined reference mapping), then no defect is detected and the cold plate passes the test. Otherwise, a defect is detected and the cold plate is identified as defective.

In addition, the entire testing process may be automated by provision of an appropriate transfer mechanism to place the cold plate within a frame of the testing apparatus aligning the cold plate to the manifold, and hence to the thermal imaging device, with the first fluid flow supply and second fluid flow supply being controlled by processor 730, which establishes the first and second fluid flows and directs obtaining of the isotherm mapping.

FIGS. 8A-8C depict one embodiment of an infrared-transparent manifold 710. In this embodiment, a second fluid flow inlet port 800 is provided in a side surface of infrared-transparent manifold 710, and a base surface 715 disposed in opposing relation to the thermal imaging device is substantially planar. As shown in FIG. 8C, second fluid flow inlet port 800 is in fluid communication with a central plenum 805 which distributes second fluid flow to a plurality of orifices 810 (e.g., jet orifices) in planar surface 713, which as noted in connection with FIG. 7, is disposed in opposing relation to the interface surface to be thermally mapped by the apparatus.

Figure 9:
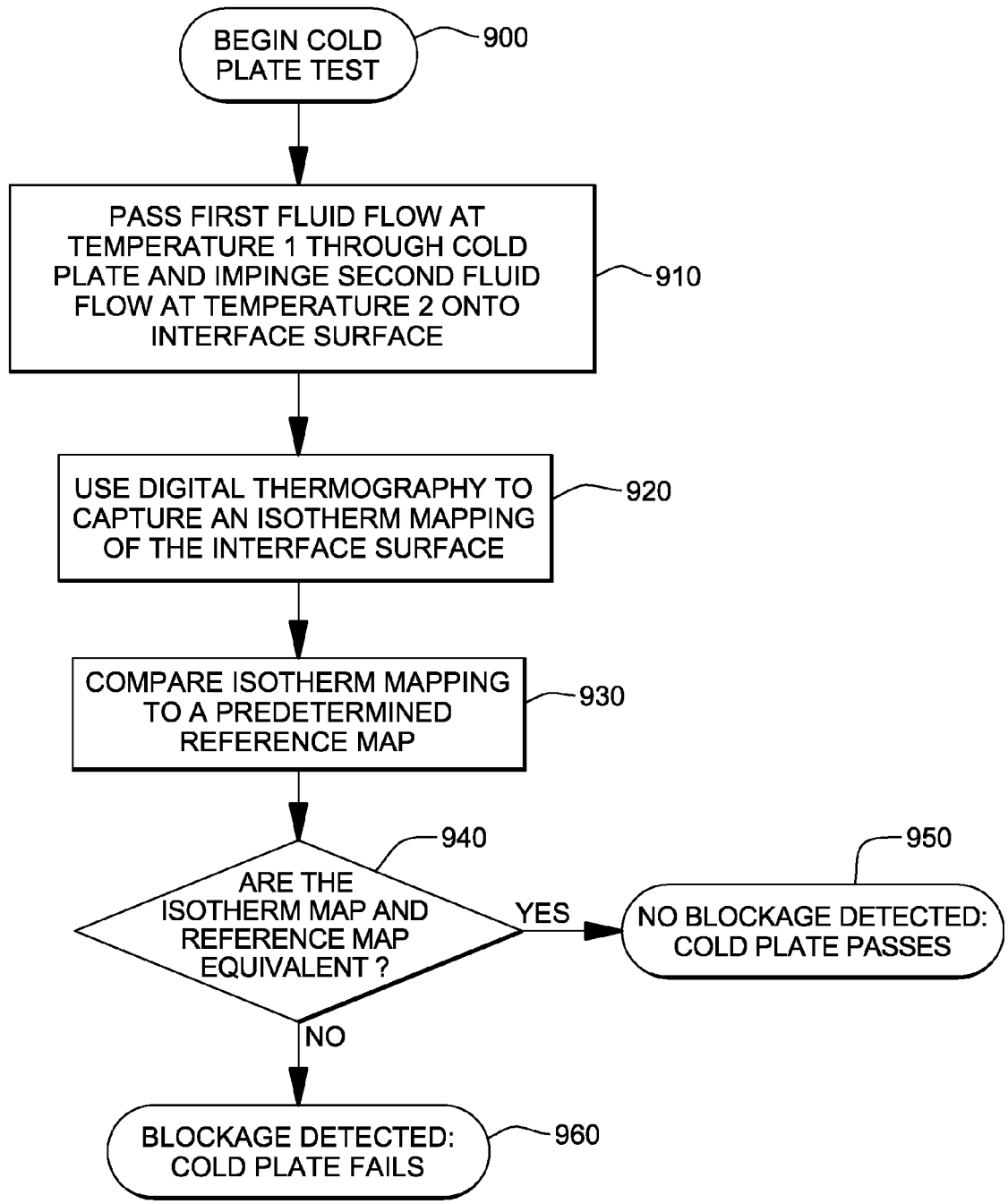
FIG. 9 is a flowchart of one embodiment of a process for detecting a defect in a cold plate, in accordance with an aspect of the present invention.

FIG. 9 depicts one embodiment of a process for testing a cold plate for a defect, in accordance with an aspect of the present invention. The cold plate test 900 begins with passing a first fluid flow at a first temperature through the cold plate and impinging a second fluid flow at a second temperature onto the interface surface thereof 910. Digital thermography is employed to capture an isotherm image (or temperature map) of the interface surface 920. This isotherm mapping is then compared to a predetermined reference map 930 and a determination is made whether the isotherm mapping and the predetermined reference map are equivalent 940. If "yes", no blockage is detected, and the cold plate passes 950. If "no", then a blockage is detected, and the cold plate is identified as defective 960.

FIG. 10A is a graph of one example of a predetermined reference isotherm map of a known good cold plate. In this example, a cold plate construction such as depicted in FIG. 6 is assumed, and the first fluid flow is a hot fluid flow, and the second fluid flow a cold fluid flow. Further, the first fluid is assumed to flow from left to right in FIG. 10A. In this simulation, the isotherm lines taken from the interface surface of the cold plate have regular contours, with temperature in the channels changing nearly linearly from the inlet to outlet plenums of the cold plate. In FIG. 10B, a blockage is detected in one or more of the channels disposed in a central portion of the cold plate. This is illustrated by the isotherm lines obtained from the interface surface of the cold plate in FIG. 10B being different in shape or contour from the isotherm lines illustrated in FIG. 10A. Note the higher regions of heat transfer at the top and bottom portions of the cold plate surface. Note also that a thermal imaging device, such as an infrared camera, is capable of picking up small differences in temperature across the interface surface. For example, a blocked channel may result in only about a 1° C. temperature difference across the interface surface, which can be readily viewed in the isotherm mapping. FIG. 10B illustrates the visual disruption of the temperature contour, which indicates location of a non-conforming channel within the cold plate, and therefore, a defect in the cold plate.

As one example, thermal analysis was performed on a highly parallel cold plate. The cold plate analyzed was assumed to be copper, with 1 mm wide channels and fins each 10 mm tall, and a 1 mm thick base (defining the interface surface of the cold plate). These are typical cold plate materials and configurations employed today. The first fluid flow was a hot fluid flow, for example, air at 5000 PA with a temperature of 50° C. flowing through the cold plate. The second fluid flow is a cold fluid flow, for example, air at 20° C., with an assumed heat transfer coefficient of 1000 impinging onto the interface surface via the infrared-transparent manifold. When no defect is present within the channels, a smooth and regular isotherm mapping such as depicted in FIG. 10A was obtained, and when a blockage is present, there was a visible disruption in the temperature contours of the mapping, indicating presence and location of one or more non-conforming, blocked channels within the cold plate. Note in this example that the cold plate under test had a thermal path between the fins in the base material with a resistance to heat flow greater than or equal to the resistance of the thermal path between the fin base and the interface surface. In other words, a cold plate with a base that is too thick or channels that are too small has significant in-plane conduction (thermal spreading), which might negatively affect the efficiency of the approach described herein.

With respect to the automated approach described above, one or more aspects thereof can be included in an article of manufacture (e.g., one or more computer program products) having, for instance, computer usable media. The media has therein, for instance, computer readable program code means or logic (e.g., instructions, code, commands, etc.) to provide and facilitate the capabilities of the present invention. The article of manufacture can be included as a part of a computer system or sold separately.

One example of an article of manufacture or a computer program product incorporating one or more aspects of the present invention is a computer program product which includes, for instance, one or more computer usable media to store computer readable program code means or logic thereon to provide and facilitate one or more aspects of the present invention. The medium can be an electronic, magnetic, optical, electromagnetic, infrared, or semiconductor system (or apparatus or device) or a propagation medium. Examples of a computer readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

A sequence of program instructions or a logical assembly of one or more interrelated modules defined by one or more computer readable program code means or logic direct the performance of one or more aspects of the present invention.

Although various embodiments are described above, these are only examples.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The capabilities of one or more aspects of the present invention can be implemented in software, firmware, hardware, or some combination thereof. At least one program storage device readable by a machine embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

Although embodiments have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A method of detecting a defect in a cold plate, the method comprising:
    establishing a first fluid flow through the cold plate, the first fluid flow being at a first temperature, wherein the cold plate is configured to facilitate cooling of an electronics component when an interface surface thereof is coupled to the electronics component and coolant is passed therethrough;
    impinging a second fluid flow onto the interface surface of the cold plate, the second fluid flow being at a second temperature, wherein the first temperature and the second temperature are different temperatures;
    obtaining an isotherm mapping of the interface surface of the cold plate while the first fluid flow passes through the cold plate and the second fluid flow impinges onto the interface surface; and
    using the isotherm mapping in determining whether the cold plate has a defect.

2. The method of claim 1, wherein impinging the second fluid flow onto the interface surface comprises employing an infrared-transparent manifold to facilitate impinging of the second fluid flow onto the interface surface of the cold plate, and wherein obtaining the isotherm mapping of the interface surface comprises obtaining the isotherm mapping of the interface surface through the infrared-transparent manifold.

3. The method of claim 2, wherein obtaining the isotherm mapping comprises infrared imaging the interface surface of the cold plate through the infrared-transparent manifold, and wherein the infrared-transparent manifold comprises a plurality of jet orifices to impinge a plurality of second fluid flow jets onto the interface surface of the cold plate.

4. The method of claim 3, wherein the first fluid flow comprises a gaseous flow.

5. The method of claim 4, wherein the second fluid flow also comprises a gaseous flow.

6. The method of claim 4, wherein the first fluid flow comprises an air flow.

7. The method of claim 1, wherein obtaining the isotherm mapping comprises utilizing digital thermography to capture the isotherm mapping of the interface surface, and wherein the method further comprises automatically comparing the isotherm mapping to a predetermined reference mapping and wherein the using comprises automatically determining from the comparing whether the isotherm mapping is equivalent to the predetermined reference mapping, and if not, identifying the cold plate as defective.

8. The method of claim 1, wherein the first fluid flow is a hot fluid flow and the second fluid flow is a cold fluid flow, and wherein the first temperature is at least 20° C. greater than the second temperature.

9. The method of claim 1, wherein the first fluid flow is a cold fluid flow and the second fluid flow is a hot fluid flow, and wherein the second temperature is at least 20° C. greater than the first temperature.

10. The method of claim 1, wherein the first fluid flow is a gaseous flow, and the second fluid flow is a gaseous flow, and wherein the temperature difference between the first temperature and the second temperature is at least 20° C.

11. The method of claim 1, wherein the isotherm mapping is an isotherm image, and the method further comprises displaying the isotherm image of the interface surface to facilitate determining whether the cold plate has a defect.

12. An apparatus for detecting a defect in a cold plate, the apparatus comprising:
    a first fluid flow supply to establish a first fluid flow through the cold plate, the first fluid flow being at a first temperature, wherein the cold plate is configured to facilitate cooling of an electronics component when an interface surface thereof is coupled to the electronics component and coolant is passed therethrough;
    a manifold configured to impinge a second fluid flow onto the interface surface of the cold plate, the second fluid flow being at a second temperature, wherein the first temperature and the second temperature are different temperatures;
    a thermal imaging device to obtain an isotherm mapping of the interface surface of the cold plate while the first fluid flow passes through the cold plate and the second fluid flow impinges onto the interface surface; and
    wherein the isotherm mapping is utilized to determine whether the cold plate has a defect.

13. The apparatus of claim 12, wherein the manifold comprises an infrared-transparent manifold, and wherein the thermal imaging device is disposed to obtain the isotherm mapping of the interface surface of the cold plate through the infrared-transparent manifold.

14. The apparatus of claim 13, wherein the thermal imaging device comprises an infrared camera, and wherein the infrared-transparent manifold comprises a plurality of jet orifices to impinge a plurality of second fluid flow jets onto the interface surface of the cold plate.

15. The apparatus of claim 14, wherein the first fluid flow comprises a gaseous flow.

16. The apparatus of claim 15, further comprising a second fluid flow supply coupled to the manifold, the second fluid flow comprising a gaseous flow.

17. The apparatus of claim 15, wherein the first fluid flow comprises an air flow.

18. The apparatus of claim 12, further comprising a processor coupled to the thermal imaging device, the processor automatically comparing the isotherm mapping to a predetermined reference mapping, and automatically determining from the comparing whether the isotherm mapping is equivalent to the predetermined reference mapping, and if not, identifying the cold plate as defective.

19. The apparatus of claim 12, further comprising a display unit coupled to the thermal imaging device for displaying the isotherm mapping to facilitate determining whether the cold plate has a defect.

20. The apparatus of claim 12, wherein one of the first fluid flow and second fluid flow is a hot fluid flow, and the other of the first fluid flow and second fluid flow is a cold fluid flow, and wherein the first temperature and the second temperature comprise a temperature difference of at least 20° C.

* * * * *